United States Patent
Kerrigan et al.

(10) Patent No.: US 9,017,988 B1
(45) Date of Patent: Apr. 28, 2015

(54) HYBRID MUSHROOM STRAIN B14528 AND DESCENDANTS THEREOF

(71) Applicant: Sylvan America, Inc., Kittanning, PA (US)

(72) Inventors: Richard W. Kerrigan, Kittanning, PA (US); Mark P. Wach, Allison Park, PA (US); Michelle E. Schultz, New Bethlehem, PA (US)

(73) Assignee: Sylvan America, Inc., Kittanning, PA (US)

( * ) Notice: Subject to any disclaimer, the term of this patent is extended or adjusted under 35 U.S.C. 154(b) by 0 days.

(21) Appl. No.: 14/186,478

(22) Filed: Feb. 21, 2014

(51) Int. Cl.
*A01H 15/00* (2006.01)
*A01G 1/04* (2006.01)

(52) U.S. Cl.
CPC . *A01H 15/00* (2013.01); *A01G 1/04* (2013.01)

(58) Field of Classification Search
None
See application file for complete search history.

(56) References Cited

U.S. PATENT DOCUMENTS 7,608,760 B2 * 10/2009 Robles et al. ............... 800/297
2010/0212042 A1 8/2010 Robles et al.

OTHER PUBLICATIONS

D.M. Beyer; Department of Plant Pathology, The Pennsylvania State University. Plant Disease—97 (1):142—Abstract; apsjournals. apsnet.org/doi/abs/10.1094/PDIS-07-12-0619-PDN; Jan. 2013, vol. 97, No. 1p. 142; 2 pages.
Richard W. Kerrigan, et al.; Meiotic Behavior and Linkage Relationships in the Secondarily Homothallic Fungus *Agaricus bisporus*; Publication Oct. 14, 1992; 12 pages.
Emmanuelle Morin, et al.; Environmental Sciences; www.pnas.org; 4146-4148, PNAS, Mar. 5, 2013, vol. 110, No. 10; 9 pages.
A.J. Velcko, Jr. et al.; Expression of Novel Genes in *Agaricus bisporus* Using an Agrobacterium-mediated Transformation Technique; 4 pages, 2004.
Micheline Imbernon, et al.; MYCOLOGIA; 88(5), 1996, pp. 749-761; BSN, the Primary Determinant of basidial spore number and reproductive mode in *Agaricus bisporus*, maps to chromosome I; 13 pages.
Callao, P., et a., 1998. Evidence for PPC1, a determinant of the pilei-pellis color of *Agaricus bisporus* fruitbodies. Fungal Genet. Biol. 23,181-188.
Foulongne-Oriol, et al., 2010. An expanded genetic linkage map of an intervarietal *Agaricus bisporus* var. *bisporus*—*A. bisporus* var. burnettii hybrid based on AFLP, SSR and CAPS markers sheds light on the recombination behaviour of the species. Fungal Genetics and Biology 47: 226-236.
Kerrigan, R.W., et al., 1993.Meiotic behavior and linkage relationships in the secondarily homothallic fungus *Agaricus bisporus*. Genetics 133, 225-236.
Loftus, M., et al., 2000. Use of SCAR marker for cap color in *Agaricus bisporus* breeding programs. Mush. Sci. 15, 201-205.
Morin, et al., 2012. Genome sequence of the button mushroom*Agaricus bisporus* reveals mechanisms governing adaptation to a humic-rich ecological niche. Proc Natl Acad Sci USA 109: 17501-17506.
Schoch, Conrad L., et al., 2012. Nuclear ribosomal internal transcribed spacer (ITS) region as a universal DNA barcode marker for Fungi. Proc. Nat. Acad. Sci. <www.pnas.org/cgi/content/short/1117018109>.
Xu, J.-P., et al. 1993. Localization of the mating type gene in *Agaricus bisporus*. App. Env. Microbiol. 59(9): 3044-3049.

* cited by examiner

*Primary Examiner* — David H Kruse
(74) *Attorney, Agent, or Firm* — Renner Kenner Greive Bobak Taylor & Weber

(57) ABSTRACT

A hybrid mushroom culture of *Agaricus bisporus*, designated as strain B14528, includes a representative culture of the strain, which has been deposited under NRRL Accession No. 50900. A method of producing a hybrid mushroom culture of *Agaricus bisporus* comprising: mating a homokaryotic line J12998-s39 with a homokaryotic line BW-s191. Additionally, mushrooms, parts of the culture and products incorporating the culture are provided.

22 Claims, No Drawings

HYBRID MUSHROOM STRAIN B14528 AND DESCENDANTS THEREOF

TECHNICAL FIELD

This invention relates to a novel class of hybrid cultures of the edible, cultivated mushroom fungus *Agaricus bisporus* (Lange) Imbach, and methods of producing and using said hybrid culture. More particularly, this invention relates to a newly developed hybrid strain designated B14528 and to cultures that are descended, or otherwise derived, from *Agaricus bisporus* strain B14528.

BACKGROUND OF THE INVENTION

The edible mushroom *Agaricus bisporus* (Lange) Imbach var. *bisporus*, a microorganism belonging to the basidiomycete fungi, is widely cultivated around the world. In Europe and North America, it is the most widely cultivated mushroom species. The value of the annual *Agaricus bisporus* mushroom crop in the United States was about $1,110,000,000 in 2012-2013, according to the National Agricultural Statistics Service, Agricultural Statistics Board, U.S. Department of Agriculture (Aug. 20, 2013).

Cultures of *Agaricus*, like those of other microorganisms, are prepared, maintained, propagated and stored on sterile media using microbiological laboratory methods. Sterile tools and aseptic techniques are used within clean rooms or sterile transfer hoods to manipulate cells of the pure cultures for various purposes including clonal propagation and for the development of new strains using diverse techniques including spore germinations on sterile growth media and controlled matings on sterile growth media. Commercial culture inocula including mushroom 'spawn' and 'casing inoculum' are also prepared using large-scale microbiological production methods, for example by aseptically introducing inoculum of a pure culture of a strain of *Agaricus bisporus* into from one to 14,000 liters of sterilized growth media under sterile conditions, and are provided to the end user as pure cultures on sterile growth media contained within sterile packaging.

Mushrooms are cultivated commercially within purpose-built structures on dedicated farms. While there are many variations on methods, the following description is typical. Compost prepared from lignocellulosic material such as straw, augmented with nitrogenous material, is finished and pasteurized within a suitable facility. Mushroom spawn, which comprises a sterilized friable 'carrier substrate' onto which a pure culture of one mushroom strain has been aseptically incorporated via inoculum and then propagated, is mixed with the pasteurized compost and is incubated for approximately 13 to about 19 days at a controlled temperature, during which time the mycelium of the mushroom culture colonizes the entire mass of compost and begins to digest it. A non-nutritive 'casing layer' of material such as peat is then placed over the compost to a depth of from about 1.5 to about 2 inches. Additional 'casing inoculum' incorporating the same mushroom culture may be incorporated into the casing layer to accelerate the formation and harvesting of mushrooms, and improve uniformity of the distribution of mycelium and mushrooms in and on the casing surface. Environmental conditions, including temperature and humidity, in the cropping facility are then carefully managed to promote and control the transition of the culture from vegetative to reproductive growth at the casing/air interface. In a further about 13 to about 18 days after casing, mushrooms will have developed to the correct stage for harvest and sale. A flush of mushrooms comprising the original culture will be picked over a 3 to 4 day period. Additional flushes of mushrooms appear at about weekly intervals. Commercially, two or three flushes of mushrooms are produced and harvested before the compost is removed and replaced in the cropping facility.

Generally speaking, strains may be differentiated on the basis of traits associated with the mushroom, such as mushroom size, mushroom shape (e.g., cap roundness, flesh thickness), color (i.e., white cap versus brown cap), surface texture (e.g., cap smoothness), tissue density and/or firmness, delayed maturation, basidial spore number greater than two, sporelessness, increased dry matter content, improved shelf life, and reduced bruising, as well as traits associated with the culture itself, and/or products incorporating the culture, and/or crops incorporating the culture, including increased crop yield, altered distribution of yield over time, decreased spawn to pick interval, resistance to infection by, symptoms of, or transmission of bacterial, viral or fungal diseases, insect resistance, nematode resistance, ease of crop management, suitability of crop for mechanical harvesting, and behavioral responses to environmental conditions including stressors, nutrient substrate composition, seasonal influences, farm practices, self/non-self interactions (compatibility or incompatibility) with various mushroom strains, to give some examples. Strains may also be differentiated based on their genotypic fingerprint (presence of specific alleles at defined marker loci in the nuclear or mitochondrial genome). Strains may have different ancestry, which will be reflected directly by the genotype, and indirectly, in some cases, by the phenotype.

Five to thirty percent of the *Agaricus* mushrooms cultivated in the United States, Europe, and elsewhere have a brown pileus color, in accordance with consumer preferences for a traditional or 'old-fashioned' product appearance. The 'portabella' mushroom market segment is supplied by the cultivation of brown-capped (=brown) strains. Market requirements for brown mushrooms in the USA and elsewhere are relatively narrow and precise for many observable phenotypic traits such as size, shape, color, color retention, firmness, and related traits such as shelf life. Consequently, genetically different strains of commercially successful brown *Agaricus bisporus* mushrooms often may not be easily differentiated on the basis of appearance of the mushrooms, which in general must conform to the market requirements.

Circa 1980, the first two white hybrid strains of *A. bisporus*, developed by a laboratory at Horst, the Netherlands, were introduced into commercial cultivation. These two "Horst" strains, called U1 and U3, are closely related hybrid strains produced by matings between two pre-existing white cultivated strains, as per M. Imbernon et al., *Mycologia*, 88(5), 749-761 (1996), herein incorporated by reference. The two parents of U1 and U3 are commercial strains belonging to two longstanding categorical types of strains known as the 'smooth-white' (SW) strains and the 'off-white' (OW) strains. The original homokaryons (or 'lines') obtained from the SW and OW strains, and used in the hybridization that produced the U1 strain, were designated H39 and H97 respectively; these cultures may no longer exist (A. Sonnenberg, pers. comm.).

However, a number of laboratories have deheterokaryotized the U1 strain and obtained neohaplont cultures incorporating one or the other nuclear type corresponding to those contributed by H39 or H97, as well as the mitochondrial type of U1. We refer to these two types of neohaplonts of U1 categorically as the SWNC and OWNC lines or homokaryons, respectively. An OWNC line designated 'H97' was deposited in the public culture collection of the Fungal Genetics Stock Center of Kansas, USA, by A. Sonnenberg, under the number 10389, and in the public collection of the American Type Culture Collection of Maryland, USA, under the number MYA-4626. The genome of H97 was sequenced and placed in the public domain by the Joint Genome Institute of California, USA. (See Morin et al. 2012, herein incorporated by reference).

One traditional type of brown-capped strain of *A. bisporus* mushroom, most often called the 'Old-Fashioned Brown' strain (or 'OFB'; examples of the OFB strain type include Sylvan's SB-65, SB-295, and RWK-2042 strains), originated as a wild strain in Europe and was the leading brown cultivar strain for many decades, even becoming the only brown cultivar in wide use in the last years of the twentieth century. A few different brown-capped hybrid strains have been developed since the 1980s, and some have enjoyed some commercial success. All publically disclosed examples of commercially relevant brown-capped hybrid strains have had both brown-capped and white-capped parents or grandparents. We refer categorically to hybrids having one white-capped parent line and one brown-capped parent line as BW, or BW-type, hybrids. This BW-type of hybrid is heteroallelic at the PPC-1 color-determining locus on Scaffold 8 of the nuclear genome. Sylvan America, Inc. developed and patented the first BW hybrid, the X618 strain (later called SC-600 and marketed as S600), a light brown strain, and later applied for patents on a class of strains including the BW hybrid J10263 strain, which is sporeless. Sylvan has developed numerous breeding lines and hybrid strains from these two, and from many other, BW-type hybrid strains, beginning in the 1980s. Others have developed and patented the BW hybrid Broncoh strain, which is light to medium brown. Yet others have developed and patented the hybrid strain BR06 (ATCC Accession No. PTA-6876, later believed to have been marketed as Heirloom), a dark brown strain that used the BW hybrid 4×29 or 4-29 strain (ATCC Accession No. PTA-6877) as a parent.

Heterokaryotic spores of an initial strain retain the great majority of the parental genotype (this behavior was shown by R. W. Kerrigan et al. in *Genetics,* 133, 225-236 (1993), herein incorporated by reference). A group of strains developed either by cloning or by spore culture, or by any other method of 'essential derivation' as discussed below, from a single progenitor (as opposed to outbreeding between two different progenitors) is called a derived lineage group. Many commercial mushroom strains developed from the OFB stock meet the criteria for Essentially Derived Varieties (as the term is applied to plant varieties).

*Agaricus bisporus* has a reproductive syndrome known as amphithallism, in which two distinct life cycles operate concurrently. As in other fungi, the reproductive propagule is a spore. *Agaricus* produces spores meiotically, on a meiosporangium known as a basidium. In a first life cycle, *A. bisporus* spores each receive a single haploid postmeiotic nucleus; these spores are competent to mate but not competent to reproduce mushrooms. These haploid spores germinate to produce homokaryotic offspring or lines which can mate with other compatible homokaryons to produce novel hybrid heterokaryons that are competent to produce mushrooms. Heterokaryons generally exhibit much less ability to mate than do homokaryons. This first lifecycle is called heteromixis, or more commonly, outbreeding. This life cycle operates but typically does not predominate in strains of *Agaricus bisporus* var. *bisporus*.

A second, inbreeding life cycle called intramixis predominates in most strains of *Agaricus bisporus* var. *bisporus*. Most spores receive two post-meiotic nuclei, and most such pairs of nuclei consist of Non-Sister Nuclear Pairs (NSNPs) which have a heteroallelic genotype at most or all centromeric-linked loci including the MAT locus. That MAT genotype determines the heterokaryotic phenotype of these offspring, which are reproductively competent and can produce a crop of mushrooms. Unusually among eukaryotes, relatively little chromosomal crossing-over is observed to have occurred in postmeiotic offspring of *A. bisporus*; empirically, very little heteroallelism (analogous to heterozygosity) is lost among heterokaryotic offspring of a heterokaryotic strain. Consequently, parental and offspring heterokaryotic genotypes and phenotypes tend to closely resemble each other, as noted above; for this reason, essential derivation, e.g., the methods of production of Essentially Derived Varieties (EDVs), is a familiar strain development technique among commercial mushroom spawn producers.

Strains currently available to the mushroom industry allow growers to produce crops of mushrooms successfully and profitably. Several factors exist that influence the degree of success and profitability achieved. Characteristics of strains that are factors which can improve producer profitability include increased productivity (higher yield or shorter cycle time), accelerated revenue capture (earlier harvest), reduced costs (for example, greater ease and speed of harvesting), reduced shrinkage (pre-sale weight loss), reduced over-weighting of product in packages (extra weight of product packaged, due to particular sizes of individual mushrooms), improved consistency of crop performance responses to variations in raw materials, growing conditions and practices, superior crop performance in particular facilities, regions, etc., reduced losses to diseases including viral, bacterial and fungal disease agents, reduced losses to insect and nematode pests of the crop. There also exist improvable properties of the mushroom product that increase consumer and marketer demand in the distribution chain, and thus increase sales volume and/or sales price, such as improved visual appeal (more desirable coloration, shape, size, or surface texture), improved or distinct flavor characteristics, improved keeping qualities (longer persistence of desirable visual attributes), etc. Thus there are many characteristics by which a novel strain might be judged as superior in a particular production facility or sales market, or in the industry regionally or globally. Thus, the need continues to exist for new hybrid strains of *Agaricus bisporus* mushroom cultures and microorganisms that provide improved characteristics for producer profitability and for improved mushroom products over other previous strains of *Agaricus bisporus*.

There is also a need for commercially acceptable brown *A. bisporus* strains with different genotypes, relative to the OFB derived lineage group and to Heirloom, for two reasons. First, strains incompatible with other strains in cultivation (such as the OFB and Heirloom strains) are known to retard the spread of viral diseases between crops of different strains. This is a particular problem for producers of brown mushrooms, which, when grown in the 'portabella' or open-cap style, release spores that can transmit virus infection throughout a facility. Second, it is well understood that when an agricultural crop industry relies extensively on a single genetic lineage (i.e., creates a commercial monoculture as once existed for the OFB lineage of *A. bisporus*, and which might exist for Heirloom), there is an increased risk of unpredictable, catastrophic crop failure on a facility-wide or industry-wide scale. Industry experiences have shown that mushroom strains, including current brown portabella strains, may be vulnerable to such risks, as discussed by Beyer et al., 2013, "First report of *Syzygites megalocarpus* (Mucorales) web mold on the commercial portabella button mushroom *Agaricus bisporus* in North America." Plant Disease 97(1): 142, herein incorporated by reference. Therefore, from a risk management and food security perspective, it is highly desirable to simultaneously provide both genetic diversification and commercially acceptable performance and crop characteristics.

SUMMARY OF THE INVENTION

The present invention is generally directed to a new and distinct *Agaricus bisporus* mushroom culture comprising the newly developed hybrid strain B14528 or Essentially Derived Varieties (EDVs) of strain B14528. A deposit of a culture of hybrid strain B14528, as disclosed herein, has been made with the Agricultural Research Services Culture Collection (NRRL) 1815 North University Street, Peoria, Ill. 61604 USA. The date of deposit was Feb. 7, 2014. The culture deposited was taken from the same culture maintained by Sylvan America, Inc., Kittanning, Pa., the assignee of record, since prior to the filing date of this application. All restrictions upon the deposit have been removed, and the deposit is intended to meet all deposit requirements of the U.S. Patent and Trademark Office, including 37 C.F.R. Sec. 1.801-1.809, and all deposit requirements under the Budapest Treaty. The NRRL Accession No. is 50900. The deposit will be maintained in the depository for a period of 30 years, or 5 years after the last request, or for the effective life of the patent, whichever is longer, and will be replaced as necessary during that period. The strain will be irrevocably and without restriction or condition released to the public upon the filing the priority application or upon the issuance of a patent on this strain according to the patent laws.

Such cultures of strain B14528 are noted to produce mushrooms, parts of mushrooms, parts of the culture, and strains and lines descended or derived from such cultures. Thus, the present invention encompasses strain B14528, Essentially Derived Varieties of strain B14528, dormant or active growing cultures present in dormant or germinating spores of strain B14528, and cultures incorporating the genetic material of strain B14528. The present invention is also directed towards methods of making and using strain B14528.

With respect to spores, living spores are heterokaryons or homokaryons in a dormant state. Spores are one part of the mushroom organism. Other parts include caps, stems, gills, cells (defined as hyphal compartments incorporating nuclei, mitochondria, cytoplasm, protoplasts, RNA, DNA, proteins, cell membranes, and cell walls including crosswalls), hyphae, and mycelium. Spores may be aseptically collected on sterile material, suspended in sterile water at various dilutions, and plated onto sterile agar growth media in order to produce germinated spores and the cultures incorporated within the spores. A preferred technique is to have within the enclosed petri plate a living *Agaricus* culture which may stimulate spore germination via the diffusion of a volatile pheromone. Germinated spores may be isolated under a microscope using sterile microtools such as steel needles, onto fresh nutrient agar plates. Using this method, heterokaryotic and homokaryotic offspring of strain B14528 comprising the spores and the cultures incorporated within the spores of strain B14528 may be obtained.

Development of novel hybrid varieties via heteromixis comprises the controlled physical association and mating of two compatible cultures to obtain a novel heterokaryon culture. Homokaryons (='lines') are the preferred starting cultures for making matings as they have maximal ability to anastomose and achieve plasmogamy with other cultures. Two heterokaryons may also be placed in physical contact but with commercially unreasonably low probabilities of a mating resulting in successful formation of a novel heterokaryon. Compatibility is determined by the genotype at the MAT locus; two homokaryons with the same MAT allele cannot establish a heterokaryon after anastomosis. In a defined mating program, homokaryotic lines are obtained and are associated in predetermined pairwise combinations. In one method, homokaryon pairs may be placed in close proximity on the surface of a nutrient agar medium in a petri dish and allowed to grow together (in a physical association), at which point anastomoses between the two cultures occur. A successful outcome is a mating. The novel hybrid heterokaryon may be obtained by transferring mycelium from the fusion zone of the dish. Such a paired mating method was used to develop the strain B14528.

In contrast, EDVs are most often derived directly from a single initial culture (e.g., strain); all such derivations produce EDVs. There is no universally accepted definition of an EDV; one example of a definition applicable to plant varieties is provided by the US Plant Variety Protection Act (revised edition, February 2006). The definition employed herein is congruent with the term as it is widely understood. 'Essential derivation' methods of obtaining cultures which are by definition consequently EDVs of a single initial culture of *A. bisporus* include somatic selection, tissue culture selection, single spore germination, multiple spore germination, selfing, repeated mating back to the initial culture, mutagenesis, and transformation, to provide some examples. DNA-mediated transformation of *A. bisporus* has been reported by Velcko, A. J. Jr., Kerrigan, R. W., MacDonald, L. A., Wach, M. P., Schlagnhaufer, C., and Romaine, C. P. 2004, Expression of novel genes in *Agaricus bisporus* using an Agrobacterium-mediated transformation technique. Mush. Sci. 16: 591-597, and references therein, herein incorporated by reference. Transformation may introduce a single new gene or allele into the genome of an initial culture.

EDVs are unambiguously recognizable by their genotype, which will be predominantly a subset of that of the single initial culture. Percentages of the initial genotype that will be present in *Agaricus bisporus* EDVs range from almost 100% in the case of somatic selections, to 99.x % in the case of strains modified by DNA-mediated transformation, to 90-99.x % in the case of single or multiple spore selections or some mutagenesis, to an average of 75-85% in the case of sibling-offspring matings (=selfing). Many methods of genotype determination, including methods described below, and others well known in the art, may be employed to determine the percentage of DNA of an initial culture that is present in another culture.

Repeated mating back to the initial culture to introgress a single trait into the genetic background of an initial culture is called introgressive trait conversion, and according to accepted definitions of EDVs, also produces an EDV of the initial culture. In a hypothetical example, in the first successive repetition of this process a resultant strain of this generation will have on average about 75% of the DNA of the initial strain while about 25% of the DNA will have been contributed by a second strain or line; as this process is repeated the DNA representation of the initial strain will increase, approaching 97% on average after 3 further successive repetitions. There is no universally accepted quantitative threshold for the proportion of DNA contributed by an initial culture in an EDV of an initial culture; we regard 75-100% genotype identity with an initial culture as indicative of an EDV of an initial culture. It is also established that an EDV of an EDV is also an EDV of an initial strain. Finally, because *Agaricus bisporus* alternates generations between heterokaryotic strains and homokaryotic lines, the criteria for essential derivation apply equally to cultures of both strains and lines.

Genotypic fingerprints are descriptions of the genotype at defined loci, where the presence of characterized alleles is recorded. Such fingerprints provide powerful and effective techniques for recognizing clones and all types of EDVs of an initial strain, as well as for recognizing ancestry within outbred lineages. Many techniques are available for defining and characterizing loci and alleles in the genotype. The most detailed approach is provided by whole-genome sequencing (WGS), which allows for direct characterization and comparison of DNA sequences across the entire genome. Using this approach to generate robust genotypic fingerprints incorporating large numbers of marker loci, it is possible to establish the nature of the relationship between two strains, including strains related by genealogical descent over several generations. Sylvan America, Inc., the inventor's assignee, has tracked genetic markers through four to six generations of its breeding pedigrees. If a sufficient number of rare markers are present in an initial strain or line, it will be possible to identify descent from an initial strain or line after several outbred generations without undue experimentation. In a hypothetical example, the mean expectation for genomic representation of an initial haploid line after 4 outbred generations is 3.1% ($50\%/2^4$) in an F4 hybrid, which corresponds to ca. 1 Mb of the nuclear genomic DNA of *A. bisporus*. Based on Sylvan America, Inc.'s analyses, that amount of DNA from each of two unrelated strains of *A. bisporus* may typically contain from about 10,000 to about 20,000 single nucleotide polymorphisms (SNPs), any one of which may provide a distinguishing marker linking the F4 hybrid to the initial line. By using multiple independent markers, ancestors of a strain can be identified with a very high probability of success and with reasonable confidence.

One trait of biological and commercial interest is heterokaryon incompatibility. The genetics of these self/non-self recognition systems are not well elucidated in basidiomycete fungi such as *Agaricus*, but are known in other genera to involve multiple alleles at multiple independent loci. Differences in the presumed genotype at the incompatibility loci prevent successful anastomoses and cytoplasmic continuity among physical mixtures of two or more heterokaryons. One consequence of such antagonistic responses is a retardation of growth and development, and a reduction of crop yield; this sort of partial crop failure is well known and evident to the experienced grower. Another consequence of heterokaryon incompatibility is restriction on the opportunity for endocellular viruses to move freely throughout or among mycelial networks. Virus diseases such as those caused by the LIV or MVX viruses can have severe negative impacts on facility productivity and must be remediated using hygiene practices which can be assisted by strain rotation. A method of improving mushroom farm hygiene called 'virus-breaking' is carried out by replacing cropping material (compost, spawn, casing inoculum) incorporating an initial strain with inoculum and cropping material incorporating another different strain that is incompatible with the initial strain. In the most effective implementation of the virus-breaking method, all biological material of the initial strain at a mushroom farm is replaced with biological material of the second, incompatible strain. Strain incompatibility creates an effective if not absolute barrier to movement of virus from biological reservoirs within a facility into new crops. Rotating cultivation usage among mushroom strains of different genotypes may also interrupt infection and infestation cycles of exogenous pests and pathogens.

As noted above, hybrid mushroom strain producers are always looking for hybrid strains that allow growers to produce crops of mushrooms successfully and profitably. In the case of strain B14528 and its derived lineage group, positive attributes documented in at least one strain thus far include a total harvested yield that may exceed that of strains like the OFB and 28Cc (which was derived as a somatic clone of Heirloom) strains, an attractive brown color and appearance, good firmness, density and piece weight, and yield timing that may be accelerated as compared to other brown strains, a trait that is particularly suitable for certain segments of the market, and which tends to accelerate revenue capture and decrease crop cycle time (potentially allowing greater throughput).

In addition, strain B14528 has a different genotype from those of both the OFB derived lineage group and of strains 28A and 28C, which, like strain 28Cc, were derived as somatic clones from Heirloom and which share its genotype and phenotype. Strain B14528 can be distinguished from all other known strains by its genotype and also by its phenotype. As expected from the novel genotype and from the pedigree, strain B14528 is incompatible with the commercially used OFB strains, and with the Heirloom-derived 28Cc strain, which is a characteristic known to retard the spread of viral diseases between strains. Thus, strain B14528 confers a potential benefit in strain rotation programs designed to manage facility hygiene. Strain B14528 has been found to simultaneously provide both genetic diversification and commercially acceptable performance and crop characteristics.

These and other advantages of the present invention over existing prior art relating to *Agaricus bisporus* mushrooms and cultures, which shall become apparent from the description which follows, are accomplished by the invention as hereinafter described and claimed.

One or more aspects of the present invention may be accomplished by a hybrid mushroom culture of *Agaricus bisporus* designated as strain 814528, a representative culture of the strain having been deposited under NRRL Accession No. 50900. The strain 814528 may include various parts of the culture, including hyphae, spores, and cells and parts of cells, including, nuclei, mitochondria, cytoplasm, protoplasts, DNA, RNA, proteins, cell membranes and cell walls, said parts being present in either the vegetative mycelium of the culture or in mushrooms produced by the culture or both. The spores may be dormant or germinated spores, and may include heterokaryons and homokaryons incorporated therein.

One or more products incorporating the hybrid mushroom culture of *Agaricus bisporus* designated as strain B14528 may be produced. Such products include mycelium, spawn, inoculum, casing inoculum, fresh mushrooms, processed mushrooms, mushroom extracts and fractions, mushroom pieces, and colonized substrates selected from grain, compost, and friable particulate matter. It will be appreciated that mushroom pieces refer to stems, pilei, and other larger portions of the mushroom itself. Spores of the mushrooms may be dormant spores or germinated spores, and may include heterokaryons and homokaryons incorporated therein.

One or more other aspects of the present invention may be accomplished by an Essentially Derived Variety of the hybrid mushroom culture of strain B14528. In one or more embodiments, an *Agaricus bisporus* culture produced by essential derivation has at least one of the essential characteristics of strain B14528, for example the same heterokaryon compatibility phenotype, and/or the further characteristics of cap roundness, flesh thickness, yield performance, and yield timing relative to commercial strains OFB and Heirloom, wherein a culture of strain B14528 has been deposited under the NRRL Accession Number 50900.

Other aspects of the present invention may be accomplished by an *Agaricus bisporus* culture having the essential physiological and morphological characteristics of strain B14528, wherein a culture of strain B14528 has been deposited under the NRRL Accession Number 50900. It will be appreciated that the physiological characteristics of the strain will include its performance characteristics as well. Still further aspects of the present invention may be accomplished by a hybrid mushroom culture of *Agaricus bisporus* having a genotypic fingerprint which has alleles at marker loci ITS, p1n150-G3-2, MFPC-1-ELF, AN, AF, and FF, wherein all of the alleles at marker loci ITS, p1n150-G3-2 MFPC-1-ELF, AN, AF, and FF of said fingerprint are present in the genotypic fingerprint of strain B14528. In one or more embodiments, the culture has a genotypic fingerprint having characters at marker loci described in Table V, wherein all of the characters of said fingerprint are present in the genotypic fingerprint of strain B14528.

Other aspects of the invention may be achieved by a method for producing a hybrid mushroom culture of *Agaricus bisporus* that includes the step of mating a homokaryotic line designated B12998-s39, a culture of which was deposited under NRRL Accession No. 50899, with a second homokaryotic line obtained from a BW-type hybrid strain. In one embodiment the second homokaryotic line obtained from a BW-type hybrid strain may be designated BW-s191, a culture of which was deposited under NRRL Accession No. 50901. Such a mating provides the hybrid mushroom culture designated strain B14528, which exhibits antagonism toward heterokaryon strains in the OFB and 28Cc/Heirloom derived lineage group. The observable heterokaryon incompatibility demonstrates the genetic distinctness of strain B14528 relative to strains like the OFB and 28Cc/Heirloom strains. In one or more embodiments, the method further includes providing a mushroom culture of the invention in mushroom products selected from the group consisting of mycelium, spawn, inoculum, casing inoculum, fresh mushrooms, processed mushrooms, parts of mushrooms, mushroom extracts and fractions, mushroom pieces, and colonized substrates selected from grain, compost, and friable particulate matter. In other embodiments, the method may include providing the mushroom culture in derived cultures selected from the group consisting of homokaryons, heterokaryons, aneuploids, somatic subcultures, tissue explant cultures, protoplasts, dormant spores, germinating spores, inbred descendents and outbred descendents, transgenic cultures, and cultures having a genome incorporating a single locus conversion.

One or more further aspects of the present invention may be accomplished by a culture, a cell or a culture including the cell, produced by the method(s) above. Thus, one or more embodiments may include a method further including the step of growing the hybrid mushroom culture to produce hybrid mushrooms and parts of mushrooms. Other embodiments may provide for methods wherein the hybrid mushroom culture produced, or the cell, includes a marker profile having alleles at marker loci ITS, p1n150-G3-2, MFPC-1-ELF, AN, AF, and FF, wherein all of the alleles at marker loci ITS, p1n150-G3-2 MFPC-1-ELF, AN, AF, and FF of said marker profile are also present in the marker profile of B14528. Still other embodiments may provide for methods wherein the hybrid mushroom culture produced, or the cell, includes a marker profile having characters at marker loci described in Table V, wherein all of the characters of said marker profile are also present in the marker profile of B14528

Finally, another aspect of the present invention may be accomplished by a method that uses the hybrid mushroom culture selected from a strain B14528 or Essentially Derived Varieties of strain B14528, a representative culture of the strain having been deposited under NRRL Accession No. 50900. In one embodiment, the method further includes growing a crop of edible mushrooms by carrying out the steps described hereinabove. In another embodiment, the method may include using strain B14528 or essentially derived varieties of strain B14528 in crop rotation to reduce pathogen pressure and pathogen reservoirs in mushroom growing facilities as described hereinabove. In yet another embodiment, the method includes using strain B14528 and Essentially Derived Varieties of strain B14528 to produce offspring as described hereinabove.

DETAILED DESCRIPTION OF THE INVENTION

Initially, in order to provide clear and consistent understanding of the specification and claims, including the scope to be given such terms, the following definitions are provided.

Allele: A heritable unit of the genome at a defined locus, ultimately identified by its DNA sequence (or by other means).

Amphithallism: A reproductive syndrome in which heteromixis and intramixis are both active.

Anastomosis: Fusion of two or more hyphae that achieves cytoplasmic continuity.

Basidiomycete: A monophyletic group of fungi producing meiospores on basidia; a member of a corresponding subdivision of Fungi such as the Basidiomycetales or Bas idiomycotina.

Basidium: The meiosporangial cell, in which karyogamy and meiosis occur, and upon which the basidiospores are formed.

Bioefficiency: For mushroom crops, the net fresh weight of the harvested crop divided by the dry weight of the compost substrate at the time of spawning, for any given sampled crop area or compost weight.

Breeding: Development of strains, lines or varieties using methods that emphasize sexual mating.

BW-type hybrid strain: A category of initial strains (and their derived lineage groups) obtained by hybridization of one white-capped parent line and one brown-capped parent line (i.e., the two lines carry alleles determining white or brown cap color, respectively, at the PPC1 locus), exemplified by SC-600, Broncoh, 4×29, J10259, J10261, J10263, and B12998; BW-type hybrid, BW strain, BW.

Cap: Pileus; part of the mushroom, the gill-bearing structure.

Cap Roundness Strictly, a ratio of the maximum distance between the uppermost and lowermost parts of the cap, divided by the maximum distance across the cap, measured on a longitudinally bisected mushroom; typically averaged over many specimens; subjectively, a 'rounded' property of the shape of the cap.

Carrier substrate: A medium having both nutritional and physical properties suitable for achieving both growth and dispersal of a culture.

Casing layer, casing: A layer of non-nutritive material such as peat or soil that is applied to the upper surface of a mass of colonized compost in order to permit development of the mushroom crop.

Casing inoculum (CI): A formulation of inoculum material incorporating a mushroom culture, typically of a defined heterokaryotic strain, suitable for mixing into the casing layer.

Cloning: Somatic propagation without selection.

Combining ability: The capacity of an individual to transmit traits or superior performance to its offspring (known and available methods of assessment vary by trait).

Compatibility: See heterokaryon compatibility.

Culture: The tangible living organism; the organism propagated on various growth media and substrates; one instance of one physical strain, line, homokaryon or heterokaryon; the sum of all of the parts of the culture, including hyphae, mushrooms, spores, cells, nuclei, mitochondria, cytoplasm, protoplasts, DNA, RNA, proteins, cell membranes and cell walls.

Derivation: Development from a strain; see Essentially Derived Variety (EDV).

Derived lineage group: An initial strain or variety and the set of EDVs derived from that single initial strain or variety.

Descent: Genealogical descent over a limited number (e.g., 10 or fewer) of generations.

Diploid: Having two haploid chromosomal complements within a single nuclear envelope.

Essential derivation: A process by which an Essentially Derived Variety is obtained from an initial variety or strain or from an EDV of an initial variety or strain; modification of an initial culture using methods including somatic selection, tissue culture selection, selfing including intramictic reproduction via single spores and multiple spores and mating of sibling offspring lines, back-mating to the initial variety, or mutagenesis and/or genetic transformation of the initial variety to produce a distinct culture in which the genotype of the resulting culture is predominantly that of the initial culture.

Essentially Derived Variety (EDV): (Note: EDV definitions incorporate elements of (1) relatedness, (2) methods of derivation, (3) and empirical tests.) In general, a variety that is predominantly derived from an initial variety or from an EDV of an initial variety, and which conforms to essential characteristics of the initial variety except for distinguishing differences resulting from the act of derivation, is an EDV of the initial variety. In the art of mushroom strain development, a strain or culture predominantly or entirely derived from a single initial strain or culture, thus having most or all, but at least 75%, of its genome or genotype present in the genome or genotype of the initial strain or culture; a strain or culture obtained from an initial strain or culture by somatic selection, tissue culture selection, selfing including mating of sibling offspring lines and intramictic reproduction via single or multiple spores, back-mating to the initial strain or culture, or mutagenesis and/or genetic transformation of the initial strain or culture; a strain or culture reconstituted from neohaplonts derived from an initial strain or culture, whether or not the haploid lines have been passed into or out of other heterokaryons; a strain or culture with the same essential phenotype as that of an initial strain or culture.

Flesh Thickness: A ratio of the maximum distance between the top of the stem and the uppermost part of the cap, divided by the maximum distance across the cap, measured on a longitudinally bisected mushroom; typically averaged over many specimens; subjectively called 'meatiness'.

Flush: A period of mushroom production within a cropping cycle, separated by intervals of non-production; the term flush encompasses the terms 'break' and 'wave' and can be read as either of those terms.

Fungus: An organism classified as a member of the Kingdom Fungi.

Genotypic fingerprint: A description of the genotype at a defined set of marker loci; the known genotype.

Gill: Lamella; part of the mushroom, the hymenophore- and basidium-bearing structure.

Haploid: Having only a single complement of nuclear chromosomes; see homokaryon.

Heteroallelic: Having two different alleles at a locus; analogous to heterozygous.

Heteroallelism: Differences between homologous chromosomes in a heterokaryotic genotype; analogous to heterozygosity.

Heterokaryon: As a term of art this refers to a sexual heterokaryon: a culture which has two complementary (i.e., necessarily heteroallelic at the Mat locus) types of haploid nuclei in a common cytoplasm, and is thus functionally and physiologically analogous to a diploid individual (but cytogenetically represented as N+N rather than 2N), and which is potentially reproductively competent, and which exhibits self/non-self incompatibility reactions with other heterokaryons; also called a strain or stock in the breeding context.

Heterokaryon compatibility: The absence of antagonism observed during physical proximity or contact between two heterokaryons that are not genetically identical; see Heterokaryon Incompatibility.

Heterokaryon incompatibility: The phenomenon of antagonism observed during physical proximity or contact between two heterokaryons that are not genetically identical; a multilocus self/non-self recognition system that operates in basidiomycete heterokaryons.

Heterokaryotic: Having the character of a heterokaryon.

Heteromixis: Life cycle involving mating between two different non-sibling haploid individuals or gametes; outbreeding.

Homoallelic: Having not more than one allele at a locus. The equivalent term in a diploid organism is 'homozygous'. Haploid lines are by definition entirely homoallelic at all non-duplicated loci.

Homokaryon: A haploid culture with a single type (or somatic lineage) of haploid nucleus (cytogenetically represented as N), and which is ordinarily reproductively incompetent, and which does not exhibit typical self/non-self incompatibility reactions with heterokaryons, and which may function as a gamete in sexually complementary anastomoses; a 'line' which, as with an inbred plant line, transmits a uniform genotype to offspring; a predominantly homoallelic line that mates well and fruits poorly is a putative homokaryon for strain development purposes; see discussion below.

Homokaryotic: Having the character of a homokaryon; haploid.

Hybrid: Of biparental origin, usually applied to heterokaryotic strains and cultures produced in controlled matings.

Hybridizing: Physical association, for example on a petri dish containing a sterile agar-based nutrient medium, of two cultures, usually homokaryons, in an attempt to achieve anastomosis, plasmogamy, and formation of a sexual heterokaryon (=mating); succeeding in the foregoing.

Hyphae: Threadlike elements of mycelium, composed of cell-like compartments.

Inbreeding: Matings that include sibling-line matings, back-matings to parent lines or strains, and intramixis; reproduction involving parents that are genetically related.

Incompatibility: See heterokaryon incompatibility.

Inoculum: A culture in a form that permits transmission and propagation of the culture, for example onto new media; specialized commercial types of inoculum include spawn and CI; plural: inocula.

Intramixis: A uniparental sexual life cycle involving formation of a complementary 'mated' pair of postmeiotic nuclei within the basidium or individual spore.

Introgressive trait conversion: mating offspring of a hybrid to a parent line or strain such that a desired trait from one strain is introduced into a predominating genetic background of the other parent line or strain.

Lamella: see 'gill'.

Line: A culture used in matings to produce a hybrid strain; ordinarily a homokaryon which is thus homoallelic, otherwise a non-heterokaryotic (non-NSNPP) culture which is highly homoallelic; practically, a functionally homokaryotic and entirely or predominantly homoallelic culture; analogous in plant breeding to an inbred line which is predominantly or entirely homozygous.

Lineage group: see 'derived lineage group'. The set of EDVs derived from a single initial strain or variety.

Locus: A defined contiguous part of the genome, homologous although often varying among different genotypes; plural: loci.

Marker assisted selection: Using linked genetic markers including molecular markers to track trait-determining loci of interest among offspring and through pedigrees.

MAT: The mating-type locus, which determines sexual compatibility and the heterokaryotic state.

Mating: The sexual union of two cultures via anastomosis and plasmogamy; methods of obtaining matings between mushroom cultures are well known in the art.

Mycelium: The vegetative body or thallus of the mushroom organism, comprised of threadlike hyphae.

Mushroom: The reproductive structure of an agaric fungus; an agaric; a cultivated food product of the same name.

Neohaplont: A haploid culture or line obtained by physically deheterokaryotizing (reducing to haploid components) a heterokaryon; a somatically obtained homokaryon.

OFB: Old-Fashioned Brown type strain; a traditional cultivar derived lineage group originating from a single initial wild strain in Europe, and also including its EDVs, exemplified by strains SB-65, SB-295, RWK__2042; OFB strain, OFB-type strain.

Offspring: Descendents, for example of a parent heterokaryon, within a single generation; most often used to describe cultures obtained from spores from a mushroom of a strain.

Outbreeding: Mating among unrelated or distantly related individuals.

Parent: An immediate progenitor of an individual; a parent strain is a heterokaryon, a parent line is a homokaryon; a heterokaryon may be the parent of an F1 heterokaryon via an intermediate parent line.

Pedigree-assisted breeding: The use of genealogical information to identify desirable combinations of lines in controlled mating programs.

Phenotype: Observable characteristics of a strain or line as expressed and manifested in an environment.

Plasmogamy: Establishment, via anastomosis, of cytoplasmic continuity leading to the formation of a sexual heterokaryon.

Progenitor: Ancestor, including parent (the direct progenitor).

Selfing: Mating among sibling lines; also intramixis.

Somatic: Of the vegetative mycelium.

Spawn: A mushroom culture, typically a pure culture of a heterokaryon, typically on a sterile substrate which is friable and dispersible particulate matter, in some instances cereal grain; commercial inoculum for compost; reference to spawn includes reference to the culture on a substrate.

Spore: Part of the mushroom, the reproductive propagule.

Stem: Stipe; part of the mushroom, the cap-supporting structure.

Sterile Growth Media: Nutrient media, sterilized by autoclaving or other methods, that support the growth of the organism; examples include agar-based solid nutrient media such as Potato Dextrose Agar (PDA), nutrient broth, and many other materials.

Stipe: see 'stem'.

Strain: A heterokaryon with defined characteristics or a specific identity or ancestry; equivalent to a variety.

Tissue culture: A de-differentiated vegetative mycelium obtained from a differentiated tissue of the mushroom.

Trait conversion: Selective introduction of the genetic determinants of one (a single-locus conversion) or more desirable traits into the genetic background of an initial strain while retaining most of the genetic background of the initial strain. See 'Introgressive trait conversion' and 'Transformation'.

Transformation: A process by which the genetic material carried by an individual cell is altered by the incorporation of foreign (exogenous) DNA into its genome; a method of obtaining a trait conversion including a single-locus conversion.

Virus-breaking: Using multiple incompatible strains, i.e. strains exhibiting heterokaryon incompatibility, successively in a program of planned strain rotation within a mushroom production facility to reduce the transmission of virus from on-site virus reservoirs into newly planted crops.

Yield: The net fresh weight of the harvest crop, normally expressed in pounds per square foot.

Yield pattern: The distribution of yield within each flush and among all flushes; influences size, quality, picking costs, and relative disease pressure on the crop and product.

With respect to the definition of homokaryon above, it is noted that homokaryons and homoallelic lines are subject to technical and practical considerations: A homokaryon in classical terms is a haploid culture which is axiomatically entirely homoallelic. In practical terms, for fungal strain development purposes, the definition is broadened somewhat to accommodate both technical limitations and cytological variation, by treating all predominately homoallelic lines as homokaryons. Technical limitations include the fact that genomes contain duplicated DNA regions including repeated elements such as transposons, and may also include large duplications of chromosomal segments due to historical translocation events; such regions may appear not to be homoallelic by most genotyping methods. Two different *A. bisporus* genomes sequenced by the Joint Genome Institute, a U.S. federal facility, differ in estimated length by 4.4%, and in gene numbers by 8.2%, suggesting a considerable amount of DNA duplication or rearrangement within different strains of the species. No presently available genome of *A. bisporus* can completely account for the physical arrangement of such elements and translocations, and so the assembled genome sequences of haploid lines may have regions that appear to be heteroallelic using currently available genotyping methods. Cytologically, a homokaryotic offspring will ordinarily be a spore that receives one haploid, postmeiotic nucleus. However, a spore receiving two third-division nuclei from the basidium will be genetically equivalent to a homokaryon. A spore receiving two second-division 'sister' postmeiotic nuclei will be a functional homokaryon even though some distal 'islands' of heteroallelism may be present due to crossovers during meiosis. Also, a meiosis that has an asymmetrical separation of homologues can produce an aneuploid, functionally homokaryotic spore in which an extra chromosome, producing a region of heteroallelism, is present. All of these cultures are highly homoallelic and all function as homokaryons. Technological limitations make it impractical to distinguish among such cultures, and also to rule out DNA segment duplication as an explanation for limited, isolated regions of the genome sequence assembly that appear to be heteroallelic. Therefore, in the present application, the use of the term 'homoallelic' to characterize a line includes entirely or predominately homoallelic lines, and cultures described in this way are functional homokaryons, are putatively homokaryotic, and are all defined as homokaryons in the present application.

Now, with respect to the invention and as noted hereinabove, the present invention relates to cultures of the hybrid *Agaricus bisporus* strain B14528 and to cultures derived or descended from B14528. Such cultures have many uses, including the production of crops of mushrooms. Thus, the present invention further relates to methods of making and using the strain B14528 and Essentially Derived Varieties (EDVs) of the strain B14528.

Hybrid strain B14528 is the product of two generations of controlled line matings by Sylvan America, Inc. The initial mating was made between the Somycel 76 strain, an OW-type strain (Somycel S.A. is a subsidiary of Sylvan) having been deposited Feb. 18, 2014 under NRRL Accession No. 50903, and wild strain BP-1, a strain deposited under ATCC Accession No. PTA-6903 and originally obtained circa 1990 by R. W. Kerrigan as director of the *Agaricus* Resource Program. See Kerrigan, R. W. 1996. "Characteristics of a large collection of wild edible mushroom germ plasm: the *Agaricus* Resource Program." pp 302-308 in Culture collections to improve the quality of life. R. A. Sampson, J. A. Stalpers, D. van der Mei, and A. H. Stouthamer, Eds. Centraalbureau voor Schimmelcultures, Baarn, The Netherlands, incorporated herein by reference. This first mating produced hybrid strain B12998. A deposit of a culture of hybrid strain B12998 has been made with the Agricultural Research Services Culture Collection (NRRL) 1815 North University Street, Peoria, Ill. 61604 USA. The date of deposit was Feb. 18, 2014. The culture deposited was taken from the same culture maintained by Sylvan America, Inc., Kittanning, Pa., since prior to the filing date of this application. All restrictions upon the deposit have been removed, and the deposit is intended to meet all deposit requirements of the U.S. Patent and Trademark Office, including 37 C.F.R. Sec. 1.801-1.809, and all deposit requirements under the Budapest Treaty. The NRRL Accession No. is 50902.

In the next generation, homokaryotic line B12998-s39, an offspring of the first hybrid, was mated with homokaryotic line BW-s191 to produce the novel hybrid strain B14528. Line BW-s191 is a unique homokaryotic line originated by Sylvan America, Inc. from a germinated spore obtained from a mushroom from a crop produced by cultivating at Sylvan a culture deposited at the American Type Culture Collection as PTA-6877, an unrestricted culture.

Cultures of strain B14528 produce commercially acceptable and desirable crops of brown mushrooms. Table I presents yield data as pounds per square foot, in four independent crop tests with internal replication. In all tests, average yields from multiple replicates are given. In test 13-247 there were two treatments of B14528 and two of two control strains, the SB-295 OFB strain and the 28Cc strain, which was derived as a somatic clone from the commercially available Heirloom strain and serves as a proxy for it. In test 13-367, average yields for one and two flushes of a crop grown as portabella mushrooms are given. As shown in Table I, productivity of strain B14528 is at least comparable to, and is typically greater than, the productivity of the SB-295 OFB and 28Cc strains, with first flush yield ranging from 83% to 167% (averaging 121%) of that of the 28Cc strain, and with total yield ranging from 105% to 145% (averaging 122%) of that of the 28Cc strain, in these four tests.

TABLE I

| Test ID | 1st flush yield | | | Total yield | | |
| --- | --- | --- | --- | --- | --- | --- |
| | B14528 | SB-295 | 28Cc | B14528 | SB-295 | 28Cc |
| 13-206 | 2.91 | 1.63 | 1.74 | 4.74 | 3.27 | 3.38 |
| 13-272 | 2.44, 2.47 | 2.02 | 2.06 | 4.88, 5.01 | 3.81 | 3.91 |
| 13-357 | 2.22 | n/a | 2.66 | 5.28 | n/a | 5.01 |
| 13-365 | 3.23 | n/a | 2.88 | 5.55 | n/a | 4.89 |

Distribution of the crop over the two- or three-flush harvest period was proportional across the tested strains, meaning that the percentage of increased yield of strain B14528 relative to the control strains was about the same in each flush. Advantageously, increased pounds of the B14528 crop typically were picked during first flush, when disease and pest pressure is lowest and product quality may be correspondingly higher.

Within first flush, the crop harvest (i.e., cumulative daily yield) was accelerated. Timing to first harvest for B14528 was about equivalent to that of the OFB and 28Cc strains (all at about 13 to 14 days after casing) in these tests. However, in the earlier days of first flush, the cumulative daily yield data in Table II, reporting averages of the 13-357 and 13-365 tests as a percentage of the control yield, shows that the harvest of strain B14528 was accelerated over that of the 28Cc control.

TABLE II

| Day (after casing): | 13 | 14 | 15 | 16 |
| --- | --- | --- | --- | --- |
| Cumulative daily yield: B14528 yield as a percent of 28Cc yield | | | | |
| 13-357 | n/a | 244% | 112% | |
| 13-365 | 124% | 258% | 252% | 152% |

In fact, within each flush, a greater proportion of the crop was harvested sooner from B14528 than from the control strains SB-295 and 28Cc. Flushes of B14528 often finished production one day earlier than did flushes of the control strains. This is advantageous in that the growing room can be emptied and refilled one day earlier when B14528 is grown, shortening the crop cycle time by about 2-3%, depending on the growing system used, and increasing facility productivity by a corresponding amount.

Cross-strain incompatibility can also be a useful commercial mushroom trait. B14528 is incompatible with both strain 28Cc, a somatic clone of Heirloom that serves as a proxy for that strain in these tests, and with the OFB derived lineage group represented by SB-295. When casing material incorporating inoculum of B14528 is placed over compost colonized with either of the other two brown strains, or conversely when either of the other two brown strains is placed over B14528, a partial crop failure ensues, demonstrating incompatibility as shown by the yield data in Table III:

TABLE III

| Spawn strain | Casing strain | Identity | First flush yield |
| --- | --- | --- | --- |
| B14528 | B14528 | Self | 2.47 lbs. |
| B14528 | SB-295 [OFB] | Non-self | 0.75 lbs. |
| B14528 | 28Cc | Non-self | 0.38 lbs. |
| SB-295 [OFB] | B14528 | Non-self | 1.01 lbs. |
| SB-295 [OFB] | SB-295 | Self | 1.92 lbs. |
| 28Cc | B14528 | Non-self | 0.58 lbs. |
| 28Cc | 28Cc | Self | 2.37 lbs. |

It will also be noted in Table III that the first break yield of B14528 in this test was somewhat higher than that of either of the other two strains in the three 'Self' pairings.

The mushrooms produced by strain B14528 have a brown pileus color. The Royal Horticultural Society (RHS) color charts indicated that the cap color of B14528 mushrooms may be described as intermediate in the range of RHS176B "moderate reddish brown" to RHS199A "moderate olive brown". Direct measurements of color of the strain B14528 mushroom cap have been made using a Minolta Chromameter and the L-a-b color space system. One measurement was made on the caps of each of ten first break mushrooms grown in a testing facility. The mean values, plus or minus the standard error, for the measured L, a, and b color components were as follows: L=64.57±0.14; a=7.60±0.05; b=24.36±0.09. Colors within or substantially coinciding with color space described by these three parameter distributions are called "brown" according to standard and accepted practices of the commercial mushroom industry.

Strain B14528 produces crops of mushrooms which may have a higher average piece weight than do mushrooms produced by the 28Cc strain or the SB-295 (OFB) strain under identical conditions. This is advantageous because heavier mushrooms cost less money to pick on a per-pound basis, increasing profitability. Table IV shows the average weight, in grams, of mushrooms grown in a single test, test 14-24, wherein all conditions except the strain were the same between treatments. Mycelium-colonized compost was used as casing inoculum for B14528 and 28Cc; a sterilized particulate casing inoculum was used for SB-295. Twenty randomly sampled mushrooms from among all mushrooms harvested on day 14 after casing (i.e., in early first break), or day 17 for SB-295 (which was slower), were weighed, and an average weight was obtained. This was repeated ten times for each strain. The average weight per mushroom was 20.8 g from the B14528 strain and 15.5 g from the 28Cc strain, and this 34% difference was statistically significant at the p=0.0007 level (t-test result). The average piece weight of mushrooms of strain SB-295 was 17.8, and this was significantly different from the B14528 value at the p=0.015 level (t-test result).

Strain B14528 produces crops of mushrooms which may have a higher average tissue density (mass/volume) than do mushrooms produced by the 28Cc or SB-295 strains under identical growing conditions. This is advantageous because denser mushrooms of equal size cost less money to pick on a per-pound basis, increasing profitability. Packaging and transportation costs may also be lower for denser mushrooms, and their keeping qualities may be superior. Table IV shows the average density, in grams/cc, of the same harvested mushroom samples grown in the test described above, test 14-24. After weighing the mushrooms as described above, the volume of each sample was determined by fluid displacement, and the average density was calculated by dividing average weight by average volume. The average density per mushroom sample was 0.69 g/cc from the B14528 strain and 0.60 g/cc from the 28Cc strain, and this 15% difference was statistically significant at the p=0.00017 level (t-test result). The average density of mushrooms of SB-295 was 0.61 and this was significantly different from the B14528 value at the $p=2.4e^{-6}$ level (t-test result).

TABLE IV

Piece weight in grams, and density in g/cc, for mushrooms of B14528, 28Cc and SB-295.

| B14528 | | | 28Cc | | | SB-295 | | |
|---|---|---|---|---|---|---|---|---|
| Weight | | | Weight | | | Weight | | |
| N = 20 | Average | Density | N = 20 | Average | Density | N = 20 | Average | Density |
| 461.0 | 23.1 | 0.678 | 314.8 | 15.7 | 0.670 | 349.1 | 17.5 | 0.572 |
| 374.8 | 18.7 | 0.646 | 330.5 | 16.5 | 0.612 | 342.3 | 17.1 | 0.606 |
| 290.5 | 14.5 | 0.760 | 337.1 | 16.9 | 0.602 | 365.2 | 18.3 | 0.619 |
| 345.7 | 17.3 | 0.691 | 291.3 | 14.6 | 0.640 | 364.0 | 18.2 | 0.612 |
| 365.8 | 18.3 | 0.677 | 375.7 | 18.8 | 0.601 | 316.4 | 15.8 | 0.597 |
| 450.7 | 22.5 | 0.668 | 314.6 | 15.7 | 0.562 | 380.6 | 19.0 | 0.634 |
| 471.4 | 23.6 | 0.669 | 316.6 | 15.8 | 0.546 | 403.2 | 20.2 | 0.611 |
| 411.1 | 20.6 | 0.685 | 222.6 | 11.1 | 0.655 | 395.6 | 19.8 | 0.604 |
| 526.7 | 26.3 | 0.671 | 321.4 | 16.1 | 0.569 | 321.8 | 16.1 | 0.596 |
| 454.4 | 22.7 | 0.777 | 284.6 | 14.2 | 0.542 | 324.4 | 16.2 | 0.624 |
| 415.2 | 20.8 | 0.69 | 310.9 | 15.5 | 0.60 | 356.3 | 17.8 | 0.61 |

The known genotypic fingerprint of strain B14528 shows numerous differences with that of the OFB and 28A and 28C Heirloom-derived strains. Data on the genotype of Heirloom, in addition to that provided in U.S. Pat. No. 7,608,760, was obtained from the analysis of cultures designated 28A and 28C, both of which were clonally derived from the commercially available Heirloom strain and which therefore also have the genotype of Heirloom. A unique fingerprint allows strain B14528 (and its Essentially Derived Varieties and descendents) to be unambiguously identified. Agronomically, genetic diversity among cultivated strains is a desirable objective because it is well established that genetic monocultures among agricultural crop species can lead to a high risk of disastrous failures due to particular disease, pest, or environmental pressures. Any otherwise desirable commercial strain with genetic novelty is therefore valuable. Strain B14528 meets those criteria.

For the purpose of this invention, the whole genomic sequence of strain B14528 and of the cultures of its parent lines and of selected EDVs of B14528 have been obtained by Sylvan America Inc. using the following method. The homokaryotic parent line cultures were grown in sterile broth growth medium after maceration. After 2-4 weeks, hyphal cells were collected by filtration, were frozen at −80C, and were lyophilized until dry. Cap tissue was obtained from mushrooms produced by cultures of the heterokaryotic B14528 strain, and was frozen and lyophilized until dry. DNA was extracted using a CTAB protocol followed by RNAse treatment and gel purification. A contractor, SeqWright, prepared DNA libraries from the DNA of each culture, and sequenced the libraries using Illumina MiSeq technology. Assemblies of the reads into genomic sequence using the public-domain reference genome sequence of H97 were performed by the contractor. Consequently about 93% to about 95% of the entire genotype of strain B14528 is known to Sylvan America, Inc. with certainty. The total number of markers distinguishing strain B14528 that are known to the assignee is, based on an analysis by a software program, to be about 750,000. A brief excerpt of the genotype of line B14528 and its parental line B12998-s39 at numerous sequence-characterized marker loci distributed at intervals along each of the 19 H97 V2.0 reference scaffolds larger than 100 Kb in length is provided in Table V.

TABLE V

| Marker: | | Culture: | |
|---|---|---|---|
| Scaffold ID | Ref Pos | OWNC (H97) | B12998-s39 | B14528 |
| scaffold_1 | 101993 | GAAGGACAT | GAAGAACAT | GAAGAACAT |
| scaffold_1 | 349966 | AAGGTGGTT | AAGGCGGTT | AAGGCGGTT |
| scaffold_1 | 660050 | TCACCATGA | TCACAATGA | TCACwATGA |
| scaffold_1 | 850014 | ATTCCTTTT | ATTCTTTTT | ATTCTTTTT |
| scaffold_1 | 1099971 | GTCGACACC | GTCGACACC | GTCGrCACC |
| scaffold_1 | 1353901 | AGATAACTA | AGATGACTA | AGATGACTA |
| scaffold_1 | 1599956 | AATAAGCGC | AATAAGCGC | AATArGCGC |
| scaffold_1 | 1850032 | CGAGTAATT | CGAGCAATT | CGAGCAATT |
| scaffold_1 | 2122001 | GGCCAGCGC | GGCCTGCGC | GGCCwGCGC |
| scaffold_1 | 2401751 | CGGATAAAT | CGGAAAAAT | CGGAwAAAT |
| scaffold_1 | 2635654 | TGCGGTTTG | TGCGATTTG | TGCGATTTG |
| scaffold_1 | 2859284 | AGGATGACT | AGGACGACT | AGGACGACT |
| scaffold_1 | 3167115 | GTCACGATT | GTCATGATT | GTCATGATT |
| scaffold_1 | 3256057 | TATCTGTTT | TCAACGTTT | TCAACGTTT |
| scaffold_2 | 128192 | TGGACCAGG | TGGAAAAGG | TGGAmmAGG |
| scaffold_2 | 350156 | TCGGGGGTG | TCGGAGGTG | TCGGrGGTG |
| scaffold_2 | 600112 | ATGTATACG | ATGTGTACG | ATGTrTACG |
| scaffold_2 | 850338 | TGGTGCTAA | TGGTTCTAA | TGGTrCTAA |
| scaffold_2 | 1099413 | CCTGACTCA | CCTGGCTCA | CCTGrCTCA |
| scaffold_2 | 1189976 | ACGGCCCAA | ACGGTCCAA | ACGGyCCAA |
| scaffold_2 | 1293936 | GTGTTTGTT | GTGTGTGTT | GTGTkTGTT |
| scaffold_2 | 1378074 | TCCACTTCA | TTAATTTCA | TCCAyTTCA |
| scaffold_2 | 1631290 | CCACTGTGC | CCACCGTGC | CCACCGTGC |
| scaffold_2 | 1643101 | CATCTTCTT | CATCGTCTT | CATCTTCTT |
| scaffold_2 | 1901773 | ACTCGAATT | ACTCAAATT | ACTCAAATT |
| scaffold_2 | 2150201 | GTCGTAGGT | GTCGAAGGT | GTCGwAGGT |
| scaffold_2 | 2389428 | GGATTTCAA | GGATGTCAA | GGATGTCAA |
| scaffold_2 | 2400520 | ATGTTATTC | ATGTCATTC | ATGTCATTC |
| scaffold_2 | 2403216 | CGAATGTTT | CGAACGTTT | CGAACGTTT |
| scaffold_2 | 2661539 | CTGCAATAA | CTGCGATAA | CTGCGATAA |
| scaffold_2 | 2914560 | GGAGGAAAG | GGAGAAAAG | GGAGAAAAG |
| scaffold_2 | 3049515 | GAAAAGCTT | GAAAGGCTT | GAAAGGCTT |
| scaffold_3 | 175472 | CTTTATTTC | CTlTTTTTC | CTTTwTTTC |
| scaffold_3 | 379203 | ATAGCGGAA | ATAGAGGAA | ATAGmGGAA |
| scaffold_3 | 614937 | CAAAATCTG | CAAATTCTC | CAAAwTCTG |
| scaffold_3 | 800122 | ACGAATAAT | ACGAGTAAT | ACGArTAAT |
| scaffold_3 | 1126997 | TCAAAGGCC | TCAAGGGCG | TCAArGGCC |
| scaffold_3 | 1296141 | ATCGGTCAT | ATCGATCAT | ATCGrTCAT |
| scaffold_3 | 1510819 | CCACTGATT | CCACAGATT | CCACwGATT |
| scaffold_3 | 1533258 | ATCACAGTT | ATCAAAGTT | ATCAAAGTT |
| scaffold_3 | 1774892 | CCGTATGGG | CCGTGTGGG | CCGTrTGG |
| scaffold_3 | 2008438 | AGCATAGCC | AGCAGAGCC | AGCAkAGCC |
| scaffold_3 | 2274053 | AAACCAAGA | AAACTAAGA | AAACyAAGA |
| scaffold_3 | 2384173 | TGACCAAGC | TGACTAAGC | TGACyAAGC |
| scaffold_4 | 126448 | GCTGTTGGT | GCTGGTGGT | GCTGkTGGT |
| scaffold_4 | 378550 | AATTTAAGC | AATCAATGC | AATywAwGC |
| scaffold_4 | 460303 | TCCTATAAC | TCCTGTAAC | TCCTrTAAC |
| scaffold_4 | 649317 | GAGGCAATG | GAGGTAATA | GAGGyAATr |
| scaffold_4 | 878923 | GTTCTGATC | GTTCCGACC | GTTCyGAyC |
| scaffold_4 | 1163185 | CAAGCTACT | CAAaaTACT | CAArmTACT |
| scaffold_4 | 1367522 | CTCTGATGT | CTCTAATGT | CTCTrATGT |
| scaffold_4 | 1607597 | AAAAATCAG | AAAAGTCAG | AAAArTCAG |
| scaffold_4 | 1889549 | ACAACAGAA | ACAACAGAA | ACAACAGAA |
| scaffold_4 | 2151161 | GTGAAACAA | GTGAAACAA | GTGAwACAA |
| scaffold_4 | 2361458 | CGGAATTTT | CGGAATTTT | CGGArTTTT |
| scaffold_5 | 87962 | GATTAAGGG | GATTAAGGG | GATTrAGGG |
| scaffold_5 | 100211 | TCCTTGAAT | TCCTTGAAT | TCCTyGAAT |
| scaffold_5 | 363169 | AATGACAAG | AATGACAAG | AATGmCAAG |
| scaffold_5 | 597097 | ATGGAAAAA | ATGGAAAAA | ATGGwAAAA |
| scaffold_5 | 851262 | TAATTCTCT | TAATTCTCT | TAATysTCT |
| scaffold_5 | 1099776 | ACATTGACA | ACATTGACA | ACATyGACA |
| scaffold_5 | 1352539 | TTGTGATCC | TTGTGATCC | TTGTkrTCC |
| scaffold_5 | 1599904 | AACTTCCTT | AACTTCCTT | AACTyCCTT |
| scaffold_5 | 1851458 | AAATAATCC | AAATAATCC | AAATwmTCC |
| scaffold_5 | 2100025 | CCCTTAGTC | CCCTTAGTC | CCCTyAGTC |
| scaffold_5 | 2278878 | GGTCGAAAA | GGTCGAAAA | GGTCGAAAA |
| scaffold_6 | 106294 | GCCATCTCG | GCCATCTCG | GCCAyCTCr |
| scaffold_6 | 106524 | TTGGAGAAC | TTGGAGAAC | TTGGAGAAC |
| scaffold_6 | 350337 | CATTTGGTT | CATTTGGTT | CATTyGGTT |
| scaffold_6 | 600047 | GGAGCATTT | GGAGCATTT | GGAGyATTT |
| scaffold_6 | 849990 | AGTTCAGGA | AGTTCAGGA | AGTTyAGGA |
| scaffold_6 | 1098535 | CAAAGATTG | CAAAGATTG | CAAArATTG |
| scaffold_6 | 1349453 | TGTCGGTAG | TGTCGGTAG | TGTCrrTAG |
| scaffold_6 | 1603456 | GCGGTACAA | GCGGTACAA | GCGGTACAA |
| scaffold_6 | 1764645 | AACCGGATT | AACCGGATT | AACCrGATT |
| scaffold_6 | 2000087 | GATTTTGCG | GATTTTGCG | GATTyTGCG |
| scaffold_6 | 2000920 | ACCTTCCAG | ACCTTCCAG | ACCTTCCAG |
| scaffold_6 | 2001839 | CTTCAATCA | CTTCAATCA | CTTCrATCA |
| scaffold_7 | 64927 | GATTCGGAG | GATTCGGAG | GATTCGGAG |
| scaffold_7 | 348994 | CCGGAGTTT | CCGGCGTTT | CCGGmGTTT |
| scaffold_7 | 600111 | CAATTATTA | CAATCATTA | CAATyATTA |
| scaffold_7 | 605781 | CGTGCTATC | CGTGTTATC | CGTGyTATC |
| scaffold_7 | 850516 | TGACGCATA | TGACGCATA | TGACrCATA |
| scaffold_7 | 873221 | AATAGACCT | AATAAACCT | AATArACCT |
| scaffold_7 | 1100248 | TCACGGAAG | TCACGGAAG | TCACrGAAG |
| scaffold_7 | 1352529 | TAAATATAT | TAAATATAT | TAAATATAT |
| scaffold_7 | 1605059 | GACAAGCAA | GACAGGCAA | GACArGCAA |
| scaffold_7 | 1944368 | AACACGGAG | AACATGGAG | AACAyGGAG |
| scaffold_8 | 350000 | ATTGACGCG | ATTGGCGCG | ATTGGCGCG |
| scaffold_8 | 606991 | GTGTATTCT | GTGTCTTCT | GTGTsTTCT |
| scaffold_8 | 834519 | ACACATAGA | ACACTTGGA | ACACwTrGA |
| scaffold_8 | 1069362 | AGCTATCCC | AGCTTTCCC | AGCTkTCCC |
| scaffold_8 | 1354068 | AGAATGCCT | AGAATGCCT | AGAAAGyyT |
| scaffold_8 | 1614036 | TTATCAGTA | TTATTAGTA | TTATyAGTA |
| scaffold_8 | 1869238 | TGGAGGTTG | TGGACGTTG | TGGAyGTTG |
| scaffold_9 | 100447 | CTATTTTCT | CTATGTTCT | CTATsTTCT |
| scaffold_9 | 350569 | AGAATATAC | AGAAAATAC | AGAArATAC |
| scaffold_9 | 611816 | GTAATCTTT | GTAAACTTT | GTAAmCTTT |
| scaffold_9 | 721973 | TGTATACGT | TGTAGACGT | TGTAGACGT |
| scaffold_9 | 1012871 | CTCATAAGA | CTCACAAGA | yTCAmAAGA |
| scaffold_9 | 1250830 | TTGTGGGGA | TTGTAGGGA | TTGTwGGGA |
| scaffold_9 | 1499265 | AGTCAGACA | AGTCCGACA | AGTCCGACA |
| scaffold_9 | 1665606 | TAAAATCTTT | TAAACTCTTT | TAAATTCTTT |
| scaffold_9 | 1676755 | CTGCCGTTT | CTGCCGTTT | CTGCwGTTT |
| scaffold_10 | 104977 | TTAGCTGGA | TTAGCTGGA | wTAGmTGGA |
| scaffold_10 | 354531 | AATCAATCA | AATCAATCA | AATCmATCA |
| scaffold_10 | 633622 | TGGGCAAAG | TGGGCAAAG | TGGGsAAAG |
| scaffold_10 | 863401 | ATAAAATTT | ATAAAATTT | ATAAAATTT |
| scaffold_10 | 1107782 | CAACCCCAC | CAACCCCAC | CAACCCCAC |
| scaffold_10 | 1338596 | GTGCATCAT | GTGCATCAT | GTGCmTCAT |
| scaffold_10 | 1477125 | ATGGTAAAT | ATGGTAAAT | ATGGwAAAw |
| scaffold_11 | 173230 | AGCGGGCGA | AGCGGGCGA | AGCGsGCGA |
| scaffold_11 | 378409 | TGATTGGGG | TGATTGGGG | TGATwGGGG |
| scaffold_11 | 627221 | TCTTCGCCC | TCTTCGCCC | TCTTyGCCC |
| scaffold_11 | 931877 | GACCTCACC | GACCTCACC | GACCkCACC |
| scaffold_11 | 1155849 | GT-TGCCAC | GT-TGCCAC | GT-/AsCCAC |
| scaffold_11 | 1250447 | GAGGCTACA | GAGGCTACA | GAGGmTACA |
| scaffold_12 | 116044 | ACGTCCTCT | ACGTGCTCT | ACGTsCTCT |
| scaffold_12 | 272255 | CCGAGTGCT | CCGAGTGCT | CCGArTGCT |
| scaffold_12 | 554582 | ACTCCGGTC | ACTCTGGTC | ACTCyGGTC |
| scaffold_12 | 770075 | GAACGTTCT | GAACATTCT | GAACrTTCT |
| scaffold_12 | 909536 | CTATGGAGG | CTATCGAGG | CTATsGAGG |
| scaffold_13 | 119283 | ACGTTACTG | ACGTTACTG | ACGTTACTG |
| scaffold_13 | 363867 | ATCCACTGC | ATCCACTGC | ATCCACTGC |
| scaffold_13 | 656215 | TTGACAAGA | TTGACAAGA | TTGACAAGA |
| scaffold_13 | 866136 | GTTGGTCAG | GTTGGTCAG | GTTGGTCAG |
| scaffold_14 | 110330 | TAGGACCAG | TAGGTCCAG | TAGGwCCAG |
| scaffold_14 | 359739 | AATTTTGAA | AATTGTGAA | AATTkTGAA |
| scaffold_14 | 603118 | GGCCCGCCT | GGCCGGCCT | GGCCsGCCT |
| scaffold_14 | 783276 | TTCGCACGT | TTCGCACGT | TTCGCACGT |
| scaffold_14 | 808308 | AAGGTATGG | AAGGTATGG | AAGGTATGG |
| scaffold_15 | 101381 | TAAACAGAT | TAAACAGAT | TAAACAGAT |
| scaffold_15 | 367204 | CCAAGATAG | CCAAGATAG | CCAAGATAG |
| scaffold_16 | 106292 | AAGCTGGAA | AAGCTGGAA | AAGCTGGAA |
| scaffold_16 | 472546 | CTTTTAATA | CTTTTAATA | CTTTTAATA |
| scaffold_17 | 107673 | GCTCTTTTA | GCTCCTTTA | GCTCsTTTA |
| scaffold_17 | 370858 | GACACAACG | GACATAACG | GACATAACG |
| scaffold_18 | 126322 | CCTCTTCCG | CCTCGTCCG | CCTCkTCCG |
| scaffold_19 | 87323 | CCCAAGCAA | CCCACGCAA | CCCAmGCAA |

Table V presents a 'fingerprint' excerpted from the SNP (Single Nucleotide Polymorphism) marker genotype of the entire genome sequences of line B12998-s39 and of the F1 hybrid B14528 strain. The IUPAC nucleotide and ambiguity codes are used to represent the observed 9-base DNA marker sequences reported above, each of which represents a genotypic marker locus. The identity of each marker locus is specified by the scaffold and SNP position information derived from the H97 V2.0 reference genome sequence published by the U.S. Department of Energy Joint Genome Institute (Morin et al. 2012). It is evident that the alleles of line B12998-s39 are incorporated within the heteroallelic genotype of the hybrid heterokaryotic strain B14528.

A brief description of the genotype of strain B14528 at further six unlinked marker loci is provided below. Because the B14528 heterokaryon incorporates two sets of chromosomes, there are two allelic copies (two characters or elements of the genotype) at each marker locus. The brief genotype excerpt provided below therefore consists of 12 alleles, characters or elements. The brief genotype excerpt was prepared by Sylvan America, Inc. using targeted Polymerase Chain Reactions to amplify genomic regions bracketing the defined markers from each of the culture DNAs. Any suitable PCR primers that bracket the defined marker regions may be used for this purpose; methods of designing and using suitable PCR primers are well known in the art. The amplified PCR product DNA was sequenced by a contractor, Eurofins, using methods of their choice, and the genotypes were determined by direct inspection of these sequences in comparison to Sylvan America's database of reference marker/allele sequences.

Description of the p1 n150-G3-2 Marker:

The 5' end of this marker segment begins at position 1 with the first "T" in the sequence TCCCAAGT, corresponding to H97 JGI V2.0 Scaffold 1 position 868615 (Morin et al. 2012) and extending in a reverse orientation (relative to the scaffold orientation) for ca. 600 nt in most alleles; an insertion of the Abr1 transposon at position 207 in the DNA of allele 1T has produced a longer segment. At present, 9 alleles incorporating at least 30 polymorphic positions have been documented from diverse strains in Sylvan America's breeding collection.

Alleles present in the B14528 immediate pedigree, or in commercially cultivated brown strains, include alleles 1T, 2, 3, and 5, characterized as follows (using the format: nucleotide base character @ alignment position, based on alignment of alleles 2, 3, and 5, and the alignable portions of allele 1T):

Allele 1T: insertion of Abr1 transposon of 320 nt @ 206^207; 'A' @ 321; 'T' @ 327; 'C' @ 374; 'G' @ 378; 'G' @ 422; 'C' @ 431; 'G' @ 472; etc.

Allele 2: no Abr1 insertion; 'A' @ 321; 'C' @ 327, 'C' @ 374; 'C' @ 378; 'G' @ 422; 'T' @ 431; 'G' @ 472; etc.

Allele 3: no Abr1 insertion; 'A' @ 321; 'T' @ 327, 'G' @ 374; 'C' @ 378; 'G' @ 422; 'T' @ 431; 'A' @ 472; etc.

Allele 5: no Abr1 insertion; 'G' @ 321; 'C' @ 327, 'C' @ 374; 'C' @ 378; 'G' @ 422; 'T' @ 431; 'G' @ 472; etc.

Because of linkage to the MAT locus, which is obligately heteroallelic in fertile heterokaryons, genotypes of all known and expected heterokaryons at p1n150-G3-2 are also heteroallelic.

The B12998-s39 homokaryon line carries allele 5. The BW-s191 homokaryon line carries allele 2. The B14528 heterokaryon strain has an '2/5' heteroallelic genotype for the p1n150-G3-2 marker locus (and also for the linked Mat locus), indicating the presence of alleles 2 and 5, which distinguishes it from the OFB strains, which have a '1T/3' genotype, and also from the 28C strain (and therefore from Heirloom, 28Cc, etc.), which has a '1T/5' genotype, and lacks allele 2, as well as from other strains which are homoallelic and/or which carry other different alleles.

Description of the ITS (=ITS1+2 region) marker:

The ITS segment is part of the nuclear rDNA region, which is a cassette that is tandemly repeated up to an estimated 100 times in the haploid genome of *A. bisporus*. Therefore there is no single precise placement of this sequence in the assembled H97 genome, and in fact it is difficult or impossible to precisely assemble the sequence over all of the tandem repeats. Three cassette copies were included on scaffold 10 of the H97 JGI V2.0 assembly, beginning at position 1612110; a partial copy is also assembled into scaffold 29 (Morin et al. 2012). The 5' end of this marker segment begins at position 1 with the first "G" in the sequence GGAAGGAT, and extending in a forward orientation (relative to the scaffold orientation) for ca. 703-704 nt in most alleles. At present, more than 9 alleles incorporating at least 11 polymorphic positions have been documented from diverse strains in Sylvan's breeding collection.

Alleles present in the B14528 immediate pedigree, or in commercially cultivated brown strains, include alleles I1, I2, I3, and I4 characterized as follows (using the format: nucleotide base character @ alignment position, based on alignment of 9 alleles).

Allele I1: 'C' @ 52; 'T' @ 461; 'T' @ 522; 'T' @ 563; etc.
Allele I2: 'T' @ 52; 'T' @ 461; 'T' @ 522; 'T' @ 563; etc.
Allele I3: 'C' @ 52; 'T' @ 461; 'C' @ 522; 'C' @ 563; etc.
Allele I4: 'C' @ 52; 'A' @ 461; 'C' @ 522; 'C' @ 563; etc.

The B12998-s39 homokaryon line carries allele I1. The BW-s191 homokaryon line carries allele I2. The B14528 heterokaryon strain has an 'I1/I2' heteroallelic genotype for the ITS marker, indicating the presence of alleles I1 and I2, which distinguishes it from the OFB strains, which have an 'I3/I4' genotype and lack alleles I1 and I2, and also from the 28C strain (and therefore from Heirloom), which has a 'I1/I1' homoallelic genotype and lacks allele I2, as well as from other strains which are homoallelic and/or which carry other different alleles.

Description of the MFPC-1-ELF Marker:

The 5' end of this marker segment begins at position 1 with the first "G" in the sequence GGGAGGGT, corresponding to H97 JGI V2.0 Scaffold 8 position 829770 (Morin et al. 2012) and extending in a forward orientation (relative to the scaffold orientation) for ca. 860 nt in most alleles. At present, at least 7 alleles incorporating at least 40 polymorphic positions have been documented from diverse strains in Sylvan's breeding collection.

Alleles present in the B14528 immediate pedigree, or in commercially cultivated brown strains, include alleles E1, E2, E3, E4, and E6, characterized as follows (using the format: nucleotide base character @ alignment position, based on alignment of 8 alleles).

Allele E1: 'A' @ 63; 'A' @ 77; 'A' @ 232; 'G' @ 301; 'A' @309; 'T' @334; 'A' @390; 'A' @ 400; 'T' @ 446, 'A' @ 481; etc.

Allele E2: 'A' @ 63; 'G' @ 77; 'A' @ 232; 'G' @ 301; 'G' @ 309; 'T' @ 334; 'G' @ 390; 'G' @ 400; 'C' @ 446, 'G' @ 481; etc.

Allele E3: 'A' @ 63; 'A' @ 77; 'A' @ 232; 'G' @ 301; 'G' @ 309; 'T' @ 334; 'A' @ 390; 'A' @ 400; 'C' @ 446, 'G' @ 481; etc.

Allele E4: 'G' @ 63; 'A' @ 77; 'A' @ 232; 'G' © 301; 'G' @ 309; 'T' @ 334; 'A' @ 390; 'A' @ 400; 'C' @ 446, 'G' @ 481; etc.

Allele E6: 'A' @ 63; 'A' © 77; 'A' @ 232; 'A' @ 301; 'G' @ 309; 'T' @ 334; 'A' @ 390; 'A' @ 400; 'C' @ 446, 'G' @ 481; etc.

The B12998-s39 homokaryon line carries allele E4. The BW-s191 homokaryon line carries allele E3. The B14528 heterokaryon strain has an 'E3/E4' heteroallelic genotype at the MFPC1-ELF marker locus, indicating the presence of alleles E3 and E4, which distinguishes it from the OFB strains, which have an 'E3/E6' genotype and lack allele E4, and also from other strains which are homoallelic and/or which carry other different alleles.

Description of the AN Marker:

The 5' end of this marker segment begins at position 1 with the first "G" in the sequence GGGTTTGT, corresponding to H97 JGI V2.0 Scaffold 9 position 1701712 (Morin et al. 2012) and extending in a forward orientation (relative to the scaffold orientation) for ca. 1660 nt (in the H97 genome) to 1700 nt (in the alignment space) in known alleles; several insertions/deletions have created length polymorphisms which, in addition to point mutations of individual nucleotides, characterize the alleles. At present, 5 alleles incorporating more than 70 polymorphic positions have been documented from diverse strains in Sylvan's breeding collection.

Alleles present in the B14528 immediate pedigree, or in commercially cultivated brown strains, include alleles N1, N2, N3, and N4, characterized in part as follows (using the format: nucleotide base character @ alignment position, based on alignment of alleles N1 through N5):

Allele N1: 'G' @ 640; [deletion] @ 844-846; 'C' @ 954; 'T' @ 882; 'A' @ 994, etc.
Allele N2: 'A' @ 640; [deletion] @ 844-846; 'C' @ 954; 'T' @ 882; 'A' @ 994, etc.
Allele N3: 'A' @ 640; [deletion] @ 844-846; 'T' @ 954; 'C' @ 882; 'G' @ 994, etc.
Allele N4: 'A' @ 640; [deletion] @ 844-846; 'C' @ 954; 'C' @ 882; 'G' @ 994, etc.

The B12998-s39 homokaryon line carries allele N3. The BW-s191 homokaryon line carries allele N4. The B14528 heterokaryon strain has an 'N3/N4' heteroallelic genotype at the AN marker locus, indicating the presence of alleles N3 and N4, which distinguishes it from the OFB strains, which have an 'N4/N4' genotype and lack allele N3, and from other strains which are homoallelic and/or which carry alleles N1 or N2 or other different alleles.

Description of the AS Marker:

The 5' end of this marker segment begins at position 1 with the first "G" in the sequence GG(T/N)GTGAT, corresponding to H97 JGI V2.0 Scaffold 4 position 752867 (Morin et al. 2012) and extending in a forward orientation (relative to the scaffold orientation) for ca. 1620 nt (in the H97 genome) to 1693 nt (in the alignment space) in known alleles; several insertions/deletions have created length polymorphisms which, in addition to point mutations of individual nucleotides, characterize the alleles. At present, 7 alleles incorporating more than 80 polymorphic positions have been documented from diverse strains in Sylvan's breeding collection.

Alleles present in the B14528 immediate pedigree, or in commercially cultivated brown strains, include alleles SC and SD, characterized in part as follows (using the format: nucleotide base character @ alignment position, based on alignment of alleles SA through SG):

Allele SA: 'C' @ 28; 'A' @ 153; [deletion] @ 258-263; 'G' @ 275; [insertion]+'TTTCCCAGC'+[insertion] @ 309-349; 'C' @ 404, etc.
Allele SC: 'T' @ 28; 'A' @ 153; 'GATATC' @ 258-263; 'G' @ 275; [insertion]+'TTTCTCAGC'+[insertion] @ 309-349; 'C' @ 404, etc.
Allele SD: 'C' @ 28; 'C' @ 153; [deletion] @ 258-263; 'T' @ 275; [deletion] @ 309-349; 'T' @ 404, etc.

The B12998-s39 homokaryon line carries allele SC. The BW-s191 homokaryon line carries allele SD. The B14528 heterokaryon has an 'SC/SD' heteroallelic genotype at the AS marker locus, indicating the presence of alleles SC and SD, which distinguishes it from strain 28C (and therefore from Heirloom), which has an 'SA/SD' genotype, and lacks allele SC, and also from other strains which are homoallelic and/or which carry allele SA or other different alleles.

Description of the FF Marker:

The 5' end of this marker segment begins at position 1 with the first "T" in the sequence TTCGGGTG, corresponding to H97 JGI V2.0 Scaffold 12 position 281674 (Morin et al. 2012) and extending in a forward orientation (relative to the scaffold orientation) for ca. 570 nt in most alleles. At present, 7 alleles incorporating at least 20 polymorphic positions have been documented from diverse strains in Sylvan's breeding collection. Alleles present in the B14528 immediate pedigree, or in commercially cultivated brown strains, include alleles FF1, FF2, and FF3, characterized as follows (using the format: nucleotide base character @ alignment position, based on alignment of alleles 1 and 2):

Allele FF1: 'CCG' @ 48-50, 'C' @ 91
Allele FF2: 'TTC' @ 48-50, 'C' @ 91
Allele FF3: 'TTC' @ 48-50, 'T' @ 91

The B12998-s39 homokaryon line carries allele FF3. The BW-s191 homokaryon line carries allele FF1. The B14528 heterokaryon strain has a heteroallelic 'FF1/FF3' genotype at the FF marker locus, indicating the presence of alleles FF1 and FF3. This distinguishes B14528 from the OFB strains, which have an 'FF1/FF2' genotype and lack allele FF3, and also from many other strains which are homoallelic and/or which carry allele FF2 or other different alleles.

In aggregate, the composite genotype of strain B14528 is novel and distinct from all other strain genotypes known to Sylvan America, Inc.

Further, the B12998-s39 parent line of B14528 has also been deposited. Specifically, a deposit of a culture of the *Agaricus bisporus* homokaryotic line B12998-s39, as disclosed herein, has been made with the Agricultural Research Services Culture Collection (NRRL) 1815 North University Street, Peoria, Ill. 61604 USA. The date of deposit was Feb. 7, 2014. The culture deposited was taken from the same culture maintained by Sylvan America, Inc., Kittanning, Pa., the assignee of record, since prior to the filing date of this application. All restrictions upon the deposit have been removed, and the deposit is intended to meet all deposit requirements of the U.S. Patent and Trademark Office, including 37 C.F.R. Sec. 1.801-1.809, and all deposit requirements under the Budapest Treaty. The NRRL Accession No. is 50899. The deposit will be maintained in the depository for a period of 30 years, or 5 years after the last request, or for the effective life of the patent, whichever is longer, and will be replaced as necessary during that period. The culture will be irrevocably and without restriction or condition released to the public upon filing of a priority application or upon the issuance of a patent according to the patent laws.

Further, the BW-s191 parent line of B14528 has also been deposited. Specifically, a deposit of a culture of the *Agaricus bisporus* homokaryotic line BW-s191, as disclosed herein, has been made with the Agricultural Research Services Culture Collection (NRRL) 1815 North University Street, Peoria, Ill. 61604 USA. The date of deposit was Feb. 7, 2014. The culture deposited was taken from the same culture maintained by Sylvan America, Inc., Kittanning, Pa., the assignee of record, since prior to the filing date of this application. All restrictions upon the deposit have been removed, and the deposit is intended to meet all deposit requirements of the U.S. Patent and Trademark Office, including 37 C.F.R. Sec. 1.801-1.809, and all deposit requirements under the Budapest Treaty. The NRRL Accession No. is 50901. The deposit will be maintained in the depository for a period of 30 years, or 5 years after the last request, or for the effective life of the patent, whichever is longer, and will be replaced as necessary during that period. The culture will be irrevocably and without restriction or condition released to the public upon filing of a priority application or upon the issuance of a patent according to the patent laws.

One use of the culture of strain B14528 is the production of crops of edible mushrooms for sale. Another use is for the improvement of facility hygiene via strain rotation and a 'virus-breaking' effect. A third use is to incorporate the genetic material of strain B14528 into offspring and derived or descended cultures including dormant and germinating spores and protoplasts. Additional uses also exist as noted above.

Hybridization of *Agaricus bisporus* cultures of the invention may be accomplished by allowing two different cultures, one of which is a genetic line present in a spore of B14528, to grow together in close proximity, preferably on sterile media, until anastomosis (i.e., hyphal or cell fusion) occurs. In a successful mating, the resultant fusion culture is a first-generation (F1) outbred hybrid culture incorporating a genetic line present in a mushroom spore which is one part of one embodiment of the present invention. Protoplasts derived from basidia or other parts of the organism are another part of the B14528 mushroom that may be used to transmit genetic material of B14528 into new cultures.

Methods for obtaining, manipulating, and mating cultures of the present invention, for producing offspring, inoculum, products, and crops of the current invention, for using a strain rotation program to improve mushroom farm hygiene, and for obtaining the genotypic fingerprint of mushroom cultures, are described hereinabove and are also well known to practitioners of the art.

In order to demonstrate practice of the invention, a culture of strain B14528 was propagated as described above to produce spawn and casing inocula, which were used to produce crops of brown mushrooms under standard commercial cultivation practices as described herein above (see Background of Invention section). Commercial culture inocula including mushroom 'spawn' and 'casing inoculum' were prepared using commercial large-scale microbiological production methods, namely, by aseptically introducing inoculum of a pure culture of strain B14528 into from one to about 2,000 liters of sterilized growth media under sterile conditions, and were disbursed into sterile packaging for test purposes. The mushroom spawn was mixed with pasteurized compost and incubated for 13 to 18 days. A non-nutritive peat-based casing layer was placed over the compost as previously described and a casing inoculum was incorporated into the casing layer. Under controlled environmental conditions, the first mushrooms reached the correct stage of development in a further 13 to 14 days after casing. The mushrooms were picked over a 3 to 4 day period. Three flushes of mushrooms were harvested before each test was concluded.

Strain B12998 is a heterokaryotic strain obtained in Sylvan America, Inc.'s strain development program. It did not have the combination of characters needed to be successful commercially; however its performance and physical characteristics approached those criteria, and the strain was assessed as having some unknown potential for further development and improvement. Consequently, B12998 was used as a parent in 329 matings to at least 10 diverse stocks of *A. bisporus*, including several different BW-type stocks, that, it was believed, might have had some useful potential in mating combinations. Individual outcomes were unpredictable and variable; it was hoped that the experiment might produce a successful result but the overall likelihood of that was considered to be low. Of the 329 novel hybrids obtained, thus far only four were of potential commercial interest, and only one, B14528, has thus far consistently met the target criteria for a successful commercial strain. It was later determined in the course of testing that strain B14528 had other beneficial attributes as well, for example incompatibility with other brown cultivar strains.

Essentially Derived Varieties of strain B14528 were obtained from single spores, multiple spore mixtures, and from tissue and somatic selections, as described hereinabove. Spores of strain B14528 were obtained and were germinated and used to produce heterokaryotic and homokaryotic offspring as described hereinabove. Homokaryotic offspring lines can be used to make matings to other lines, and further hybrids can be obtained from these matings. Spawn and casing inoculum of B14528, 28Cc, and OFB strain SB-295, were used in self/self and self/non-self combinations in test crops to confirm the incompatibility of the two strains, a prerequisite for use in virus-breaking strategies, all as described hereinabove.

Although the invention has been described in terms of particular embodiments in this application, one of ordinary skill in the art, in light of the teachings herein, can generate additional embodiments and modifications without departing from the spirit of, or exceeding the scope of, the claimed invention. Accordingly, it is understood that the descriptions herein are proffered only to facilitate comprehension of the invention and should not be construed to limit the scope thereof.

What is claimed is:

1. A hybrid mushroom culture of *Agaricus bisporus* designated as strain B14528, a representative culture of the strain having been deposited under NRRL Accession No. 50900.

2. A part of the hybrid mushroom culture of claim 1 selected from the group consisting of hyphae, spores, and cells and parts of cells, selected from nuclei, and protoplasts.

3. The part of the hybrid mushroom culture of claim 2, wherein the spores are selected from dormant and germinated spores, and wherein the dormant and germinated spores include heterokaryons and homokaryons.

4. A product comprising the hybrid mushroom culture of *Agaricus bisporus* designated as strain B14528 of claim 1, the product selected from the group consisting of mycelium, spawn, inoculum, casing inoculum, fresh mushrooms, processed mushrooms, mushroom pieces, and colonized substrates including grain, compost, and friable particulate matter.

5. An Essentially Derived Variety of the hybrid mushroom culture of claim 1, wherein said Essentially Derived Variety is a culture of a strain derived from a single initial culture of strain B14528, wherein a culture of the strain B14528 has been deposited under NRRL Accession Number 50900, such that at least 75%, of its genome or genotype is present in the genome or genotype of the initial culture of strain B14528.

6. A hybrid mushroom culture of *Agaricus bisporus* having a genotypic fingerprint which has alleles at marker loci ITS, p1n150-G3-2, MFPC-1-ELF, AS, AF, and FF, wherein all of the alleles at marker loci ITS, p1n150-G3-2, MFPC-1-ELF, AN, AF, and FF of said fingerprint are present in the genotypic fingerprint of strain B14528, wherein a culture of strain B14528 has been deposited under the NRRL Accession Number 50900.

7. The hybrid mushroom culture of claim 6, wherein said culture has a genotypic fingerprint which has allelic characters at marker loci described in a column labeled B14528 of Table V, wherein all of the allelic characters of said fingerprint are present in the genotypic fingerprint of strain B14528, wherein a culture of strain B14528 has been deposited under the NRRL Accession Number 50900.

8. An *Agaricus bisporus* culture having all of the physiological and morphological characteristics of strain B14528, wherein a culture of strain B14528 has been deposited under the NRRL Accession Number 50900.

9. A method of producing a hybrid mushroom culture of *Agaricus bisporus* comprising mating a homokaryotic line B12998-s39, a culture of which has been deposited under NRRL Accession No. 50899, with a homokaryotic line obtained from a BW-type hybrid strain.

10. The method of claim 9, wherein the homokaryotic line obtained from a BW-type hybrid strain is a homokaryotic line BW-s191.

11. The method according to claim 9, wherein said hybrid mushroom culture exhibits antagonism toward heterokaryon strains in the OFB and Heirloom derived lineage groups.

12. The method according to claim 9, further comprising: providing the mushroom culture in mushroom products selected from the group consisting of mycelium, spawn, inoculum, casing inoculum, fresh mushrooms, processed mushrooms, parts of mushrooms, mushroom pieces, and colonized substrates including grain, compost, and friable particulate matter.

13. The method according to claim 9, further comprising: providing the mushroom culture in derived cultures selected from the group consisting of homokaryons, heterokaryons, aneuploids, somatic subcultures, tissue explants cultures, protoplasts, dormant spores, germinating spores, inbred descendents and outbred descendents, transgenic cultures, and cultures having a genome incorporating a single locus conversion.

14. A culture produced by the method of claim 9.

15. The method of claim 9, further comprising growing the hybrid mushroom culture to produce hybrid mushrooms and parts of mushrooms.

16. The method of claim 9, wherein the hybrid mushroom culture produced comprises a marker profile having alleles at marker loci ITS, p1n150-G3-2, MFPC-1-ELF, AS, AF, and FF, wherein all of the alleles at marker loci ITS, p1n150-G3-2, MFPC-1-ELF, AS, AF, and FF of said marker profile are also present in the marker profile of B14528, wherein a culture of strain B14528 has been deposited under the NRRL Accession Number 50900.

17. A cell of the hybrid culture produced by the method of claim 9.

18. The cell of claim 17, further comprising a marker profile having alleles at marker loci ITS, p1n150-G3-2, MFPC-1-ELF, AS, AF, and FF, wherein all of the alleles at marker loci ITS, p1n150-G3-2, MFPC-1-ELF, AS, AF, and FF of said marker profile are also present in the marker profile of strain B14528, wherein a culture of strain B14528 has been deposited under NRRL Accession Number 50900.

19. The cell of claim 17, further comprising a marker profile having allelic characters at marker loci described in a column labeled B14528 of Table V, wherein all of the allelic characters of said marker profile are also present in the marker profile of strain B14528, wherein a culture of strain B14528 has been deposited under NRRL Accession Number 50900.

20. A culture comprising the cell of claim 17.

21. An Essentially Derived Variety of the hybrid mushroom culture of claim 1, wherein said Essentially Derived Variety is a culture of a strain derived from an Essentially Derived Variety of a single initial culture of strain B14528, wherein a culture of the strain B14528 has been deposited under NRRL Accession Number 50900, such that at least 75%, of its genome or genotype is present in the genome or genotype of the initial culture of strain B14528.

22. An Essentially Derived Variety of the hybrid mushroom culture of claim 1, wherein at least 75% of the genome or genotype of said Essentially Derived Variety is present in the genome or genotype of the initial culture of strain B14528, wherein a culture of the strain B14528 has been deposited under NRRL Accession Number 50900.

* * * * *